(12) United States Patent
Coggan et al.

(10) Patent No.: US 7,402,346 B2
(45) Date of Patent: Jul. 22, 2008

(54) ORGANIC ELECTROLUMINESCENT DEVICES

(75) Inventors: Jennifer A. Coggan, Cambridge (CA); Hany Aziz, Oakville (CA); Timothy P. Bender, Port Credit (CA); Nan-Xing Hu, Oakville (CA)

(73) Assignee: LG. Philips LCD Co., Ltd., Seoul (KR)

( * ) Notice: Subject to any disclaimer, the term of this patent is extended or adjusted under 35 U.S.C. 154(b) by 385 days.

(21) Appl. No.: 11/006,000

(22) Filed: Dec. 7, 2004

(65) Prior Publication Data

US 2006/0121311 A1 Jun. 8, 2006

(51) Int. Cl.
*H01L 51/54* (2006.01)
*C09K 11/06* (2006.01)
*C07C 13/573* (2006.01)

(52) U.S. Cl. .................. 428/690; 428/917; 313/504; 313/506; 257/40; 257/E51.049; 585/26

(58) Field of Classification Search .................. None
See application file for complete search history.

(56) References Cited

U.S. PATENT DOCUMENTS

| | | | |
|---|---|---|---|
| 3,172,862 A | 3/1965 | Gurnee et al. |
| 4,356,429 A | 10/1982 | Tang |
| 4,539,507 A | 9/1985 | VanSlyke et al. |
| 4,720,432 A | 1/1988 | VanSlyke et al. |
| 4,769,292 A | 9/1988 | Tang et al. |
| 4,885,211 A | 12/1989 | Tang et al. |
| 5,059,861 A | 10/1991 | Littman et al. |
| 5,141,671 A | 8/1992 | Bryan et al. |
| 5,150,006 A | 9/1992 | Van Slyke et al. |
| 5,151,629 A | 9/1992 | VanSlyke |
| 5,227,252 A | 7/1993 | Murayama et al. |

(Continued)

FOREIGN PATENT DOCUMENTS

EP 0 681 019 11/1995

(Continued)

OTHER PUBLICATIONS

Machine translation, JP 2004-224766, Inoue et al.*

(Continued)

*Primary Examiner*—Terrel Morris
*Assistant Examiner*—Brett A Crouse
(74) *Attorney, Agent, or Firm*—McKenna Long & Aldridge LLP

(57) ABSTRACT

An organic electroluminescent device comprising an anode, an electroluminescent region, and a cathode. The luminescent region comprises a light-emitting material of Formula I

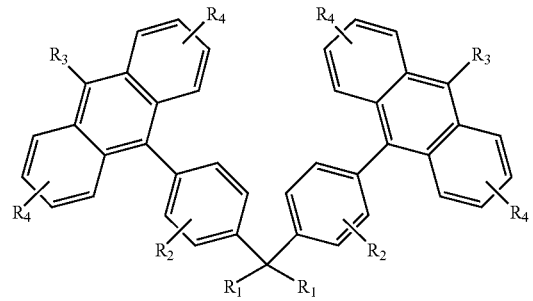

wherein $R_1$ is independently selected from the group consisting of a hydrogen, an alkyl group, an aryl group, a heteroaryl group, an alkoxy group, an amino group, an alkyl amino group, and an aryl amino group; $R_2$ is independently selected from the group consisting of hydrogen, a hetero atom, and an alkyl group; $R_3$ is independently selected from the group consisting of hydrogen, an alkyl group, an aryl group, a heteroaryl group, an alkoxy group, a halogen atom, and a cyano group; and, $R_4$ is independently selected from the group consisting of hydrogen, an alkyl group, an aryl group, a heteroaryl group, an alkoxy group, a halogen atom, and a cyano group.

13 Claims, 3 Drawing Sheets

U.S. PATENT DOCUMENTS

| | | | |
|---|---|---|---|
| 5,276,381 A | 1/1994 | Wakimoto et al. | |
| 5,429,884 A | 7/1995 | Namiki et al. | |
| 5,457,565 A | 10/1995 | Namiki et al. | |
| 5,516,577 A | 5/1996 | Matsuura et al. | |
| 5,593,788 A | 1/1997 | Shi et al. | |
| 5,601,903 A | 2/1997 | Fujii et al. | |
| 5,608,287 A | 3/1997 | Hung et al. | |
| 5,635,308 A * | 6/1997 | Inoue et al. | 428/696 |
| 5,703,436 A | 12/1997 | Forrest et al. | |
| 5,728,801 A | 3/1998 | Wu et al. | |
| 5,739,635 A | 4/1998 | Wakimoto | |
| 5,846,666 A | 12/1998 | Hu et al. | |
| 5,853,905 A | 12/1998 | So et al. | |
| 5,925,472 A | 7/1999 | Hu et al. | |
| 5,925,980 A | 7/1999 | So et al. | |
| 5,935,720 A | 8/1999 | Chen et al. | |
| 5,942,340 A | 8/1999 | Hu et al. | |
| 5,952,115 A | 9/1999 | Hu et al. | |
| 6,057,048 A | 5/2000 | Hu et al. | |
| 6,114,055 A | 9/2000 | Choong et al. | |
| 6,130,001 A | 10/2000 | Shi et al. | |
| 6,225,467 B1 | 5/2001 | Esteghamatian et al. | |
| 6,229,012 B1 | 5/2001 | Hu et al. | |
| 6,392,250 B1 | 5/2002 | Aziz et al. | |
| 6,392,339 B1 | 5/2002 | Aziz et al. | |
| 6,614,175 B2 | 9/2003 | Aziz et al. | |
| 6,765,348 B2 | 7/2004 | Aziz et al. | |
| 6,777,111 B1 | 8/2004 | Tanaka et al. | |
| 2002/0132134 A1 * | 9/2002 | Hu et al. | 428/690 |
| 2002/0180349 A1 | 12/2002 | Aziz et al. | |
| 2003/0234609 A1 | 12/2003 | Aziz et al. | |
| 2006/0055305 A1 | 3/2006 | Funahashi et al. | |

FOREIGN PATENT DOCUMENTS

| | | |
|---|---|---|
| EP | 1 385 221 | 1/2004 |
| JP | 2004-171828 | 6/2004 |
| JP | 2004-224766 | 8/2004 |

OTHER PUBLICATIONS

European Search Report dated Apr. 18, 2006.

* cited by examiner

ORGANIC ELECTROLUMINESCENT DEVICES

BACKGROUND

Illustrated herein, in various exemplary embodiments, are organic electroluminescent (EL) devices, and more specifically, organic EL devices with a number of excellent performance characteristics inclusive of the enablement of blue emitting EL devices. These devices contain luminescent components or a luminescent component with excellent high thermal stability, film forming characteristics and intense blue fluorescence. Organic EL devices are desired that are capable of providing uniform luminescence, saturated color especially in the blue regions of the visible spectrum, and low driving voltages. The organic EL devices disclosed herein enable, in embodiments, the above characteristics and contain organic luminescent materials or light emitting components comprised of fluorescent hydrocarbon compounds. The devices can be selected for use, for example, in flat-panel emissive display technologies, including TV screens, computer screens, and the like.

BRIEF DESCRIPTION

In accordance with one aspect, the present disclosure provides a light-emitting material of the formula

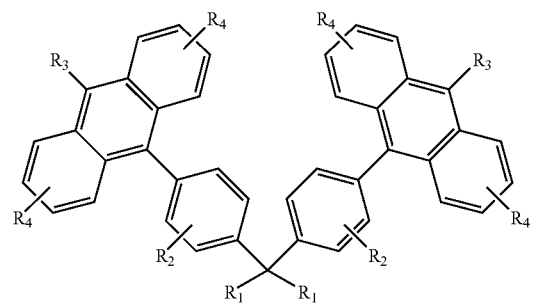

wherein $R_1$ is independently selected from the group consisting of a hydrogen, an alkyl group, an aryl group, a heteroaryl group, an alkoxy group, an amino group, an alkyl amino group, and an aryl amino group; $R_2$ is independently selected from the group consisting of hydrogen, a hetero atom, and an alkyl group; $R_3$ is independently selected from the group consisting of hydrogen, an alkyl group, an aryl group, a heteroaryl group, an alkoxy group, a halogen atom, and a cyano group; and, $R_4$ is independently selected from the group consisting of hydrogen, an alkyl group, an aryl group, a heteroaryl group, an alkoxy group, a halogen atom, and a cyano group.

In another aspect, disclosed herein is an organic light-emitting device (OLED) comprising an anode, a cathode, and an eluminescent region disposed between said anode and said cathode, said eluminescent comprising a light-emitting material of the formula

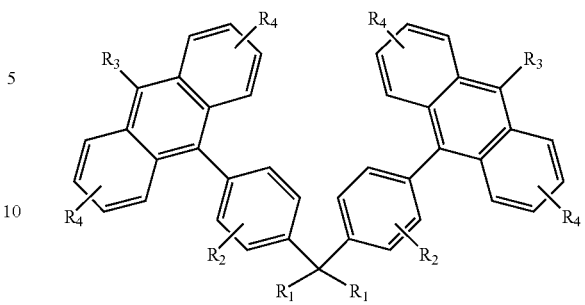

wherein $R_1$ is independently selected from the group consisting of a hydrogen, an alkyl group, an aryl group, a heteroaryl group, an alkoxy group, an amino group, an alkyl amino group, and an aryl amino group; $R_2$ is independently selected from the group consisting of hydrogen, a hetero atom, and an alkyl group; $R_3$ is independently selected from the group consisting of hydrogen, an alkyl group, an aryl group, a heteroaryl group, an alkoxy group, a halogen atom, and a cyano group; and, $R_4$ is independently selected from the group consisting of hydrogen, an alkyl group, an aryl group, a heteroaryl group, an alkoxy group, a halogen atom, and a cyano group.

In yet another aspect, the present disclosure provides a display device comprising a first electrode; a second electrode; and a luminescent region disposed between said first and said second electrode, said luminescent region comprising a first charge transport layer, light-emitting layer, and a second charge transport layer, wherein said light-emitting layer comprises a light emitting material of the Formula I

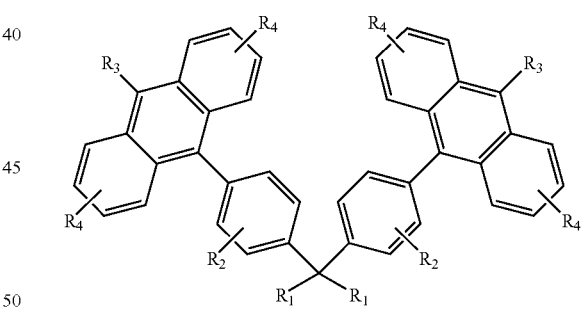

wherein $R_1$ is independently selected from the group consisting of a hydrogen, an alkyl group, an aryl group, a heteroaryl group, an alkoxy group, an amino group, an alkyl amino group, and an aryl amino group; $R_2$ is independently selected from the group consisting of hydrogen, a hetero atom, and an alkyl group; $R_3$ is independently selected from the group consisting of hydrogen, an alkyl group, an aryl group, a heteroaryl group, an alkoxy group, a halogen atom, and a cyano group; and, $R_4$ is independently selected from the group consisting of hydrogen, an alkyl group, an aryl group, a heteroaryl group, an alkoxy group, a halogen atom, and a cyano group.

These and other non-limiting aspects and/or objects of the development are more particularly disclosed below.

BRIEF DESCRIPTION OF THE DRAWINGS

The following is a brief description of the drawings, which are presented for the purposes of illustrating the development disclosed herein and not for the purposes of limiting the same.

DETAILED DESCRIPTION

The disclosure relates to organic electroluminescent devices, such as, for example, OLEDs, comprising a first electrode, a second electrode, and an eluminescent region disposed between the first and second electrode. The first and second electrode may be one of an anode or a cathode. The illuminescent region comprises a light-emitting compound of Formula I

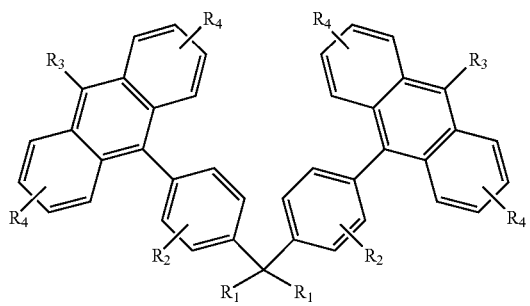

wherein $R_1$ is independently selected from the group consisting of a hydrogen, an alkyl group, an aryl group, a heteroaryl group, an alkoxy group, an amino group, an alkyl amino group, and an aryl amino group; $R_2$ is independently selected from the group consisting of hydrogen, a hetero atom, and an alkyl group; $R_3$ is independently selected from the group consisting of hydrogen, an alkyl group, an aryl group, a heteroaryl group, an alkoxy group, a halogen atom, and a cyano group; and, $R_4$ is independently selected from the group consisting of hydrogen, an alkyl group, an aryl group, a heteroaryl group, an alkoxy group, a halogen atom, and a cyano group.

Figure 1:
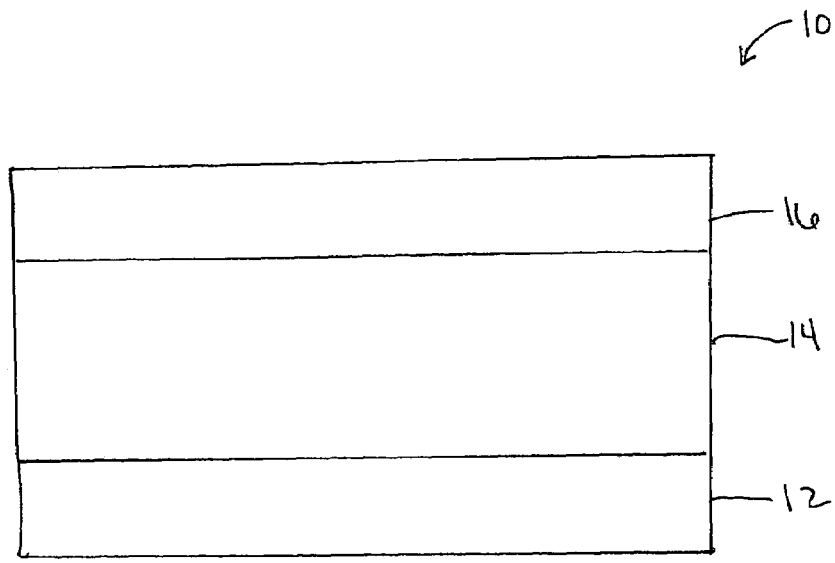
FIG. 1 is a schematic cross-sectional view of an OLED according to a first exemplary embodiment.

A first exemplary embodiment of an organic electroluminescent device is shown in FIG. 1. OLED 10 comprises an anode 12, a luminescent region 14, and a cathode 16. The luminescent region 14 comprises a light-emitting material of Formula I.

Figure 2:
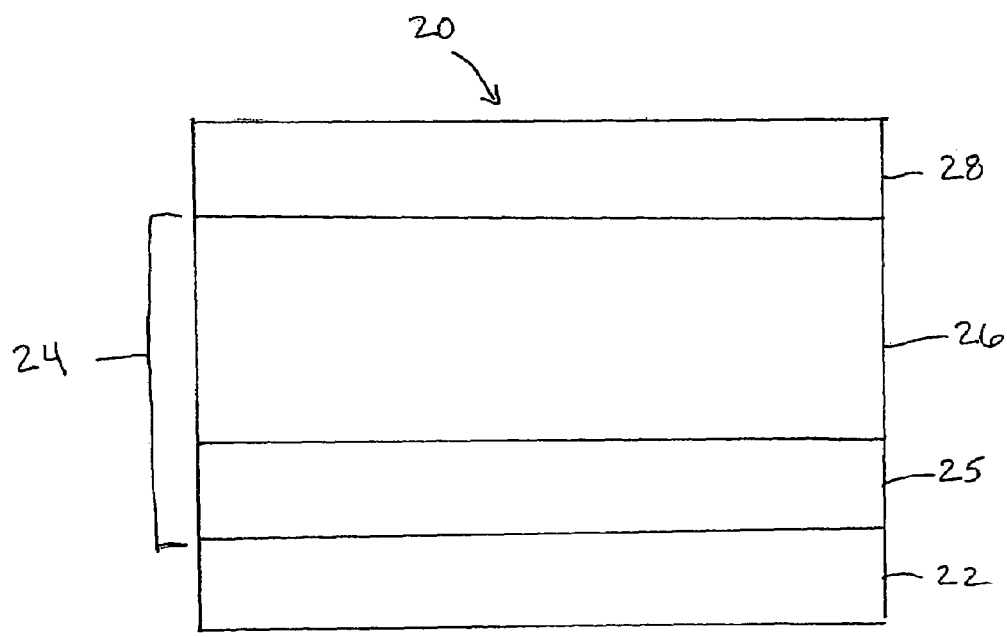
FIG. 2 is a schematic cross-sectional view of an OLED according to a second exemplary embodiment.

With reference to FIG. 2, a second exemplary embodiment of an organic electroluminescent device is shown. In FIG. 2, OLED 20 comprises a first electrode 22, a luminescent region 24, and a second electrode 28. Luminscent region 24 comprises light-emitting layer 25 and charge transport layer 26. In one embodiment, the first electrode can be the cathode, while the second electrode can be the anode. In an alternative embodiment, the first electrode can be the anode, while the second electrode can be the cathode. When the second electrode is an anode, the charge transport layer 26 can be a hole transporting layer. Alternatively, when the second electrode is a cathode, the charge transport layer 26 can be an electron transporting layer. Light-emitting layer 25 comprises a light-emitting material of Formula I.

Figure 3:
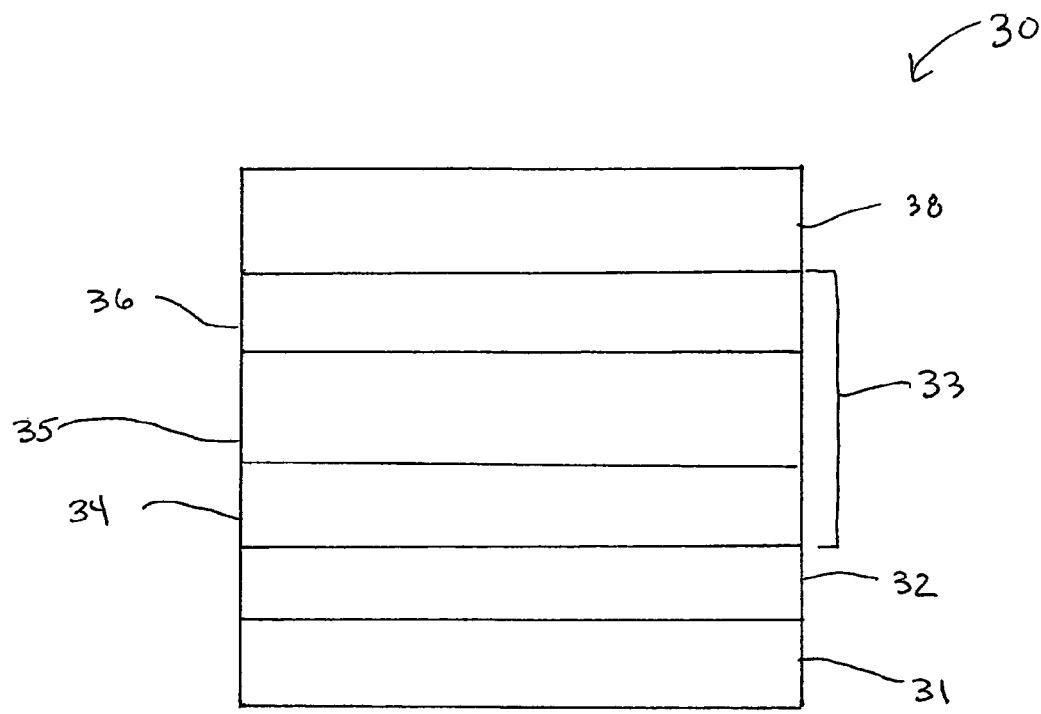
FIG. 3 is a schematic cross-sectional view of an OLED according to a third exemplary embodiment.

A third exemplary embodiment of an organic electroluminescent device is depicted in FIG. 3. In FIG. 3, OLED 30 comprises an anode 31, an optional buffer layer 32, a luminescent region 33, and a cathode 38. Luminescent region 33 comprises a hole transport layer 34, a light-emitting layer 35, and an electron transport layer 36. Light-emitting layer 35 comprises a light-emitting material of Formula I.

Figure 4:
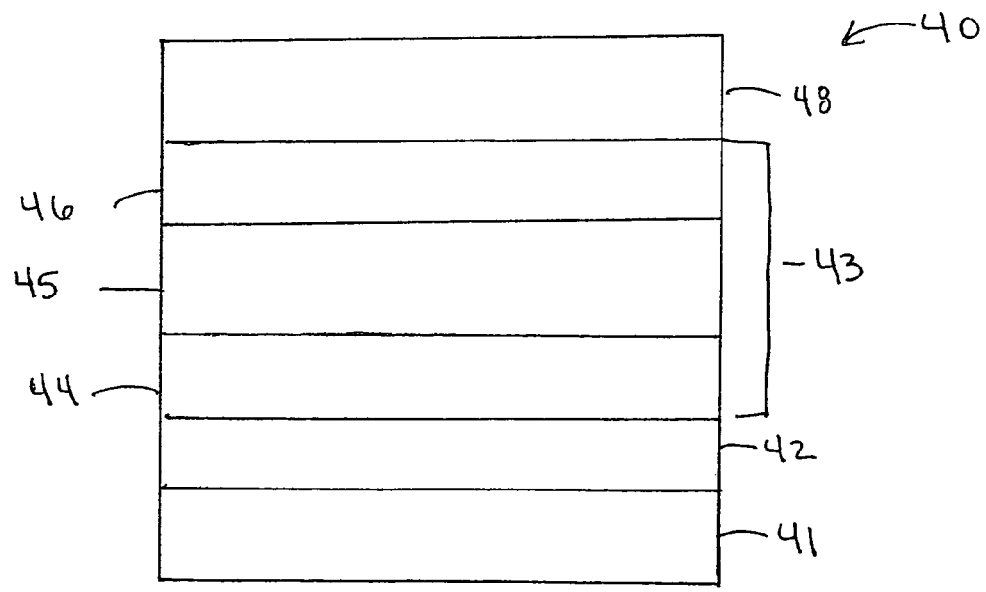
FIG. 4 is a schematic cross-sectional view of a display device according to a fourth exemplary embodiment.

With reference to FIG. 4, display device 40, such as, for example, an OLED, comprises a first electrode 41, an optional buffer layer 42, a luminescent region 43, and a second electrode 48. Luminescent region 43 comprises a first charge transport layer or zone 44, a light-emitting layer 45, and a second charge transport zone 46. The light-emitting layer 45 comprises a light-emitting material of the Formula I. The first electrode can be either an anode or a cathode, and the second electrode can be either a cathode or an anode. Additionally, the first charge transport zone can be either a hole transport zone when the first electrode is an anode (the second charge transport zone being an electron transport zone) or an electron transport when the first electrode is a cathode (the second charge transport zone being a hole transport zone).

It will be appreciated that the organic electroluminescent devices depicted in FIGS. 1-3 may further comprises a substrate positioned at any suitable location in the depicted OLED. For example, the respective devices may include a substrate in contact with either the first or second electrode, i.e., with either the anode or the cathode.

It will also be appreciated that each layer of an organic electroluminescent device may comprise a single layer or two, three, four or more layers. For purposes of the present disclosure, adjacent layers are considered separate if the composition of the layers differs in at least one of i) the concentrations of the components in the layers and/or ii) the components making up the compositions of the respective layers. For example, adjacent layers having compositions comprising the same components but at different concentrations are considered separate layers. The term "region" refers to a single layer, a plurality of layers such as two, three, or more layers, and/or one or more zones. The term "zone" refers to a single layer, a plurality of layers, a single functional area in a layer, or a plurality of functional areas in a layer.

The luminescent region of an organic electroluminescent device according to the present disclosure, including, for example, a light-emitting layer, comprises a light-emitting material of Formula I

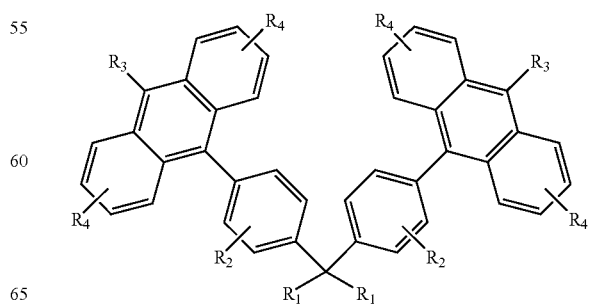

wherein R₁ is independently selected from the group consisting of a hydrogen, an alkyl group, an aryl group, a heteroaryl group, an alkoxy group, an amino group, an alkyl amino group, and an aryl amino group; R₂ is independently selected from the group consisting of hydrogen, a hetero atom, and an alkyl group; R₃ is independently selected from the group consisting of hydrogen, an alkyl group, an aryl group, a heteroaryl group, an alkoxy group, a halogen atom, and a cyano group; and, R₄ is independently selected from the group consisting of hydrogen, an alkyl group, an aryl group, a heteroaryl group, an alkoxy group, a halogen atom, and a cyano group.

In embodiments, R₁ is independently selected from the group consisting of a hydrogen, an alkyl group having 1 to about 10 carbon atoms, an aryl group having about 6 to about 30 carbon atoms, a heteroaryl group of from about 5 to about 24 carbon atoms, and an alkoxy group having 1 to about 24 carbon atoms; R₂ is independently selected from the group consisting of hydrogen, a hetero atom such as, for example, nitrogen, sulfur, or oxygen, and an alkyl group having 1 to about 10 carbon atoms; and R₃ is independently selected from the group consisting of hydrogen, an alkyl group having 1 to 10 carbon atoms, an aryl group having about 6 to about 30 carbon atoms, and heteroaryl group having about 5 to about 24 carbon atoms, and an alkoxy group having 1 to about 24 carbon atoms.

Examples of suitable alkyl groups for one or each of R₁, R₂, or R₃ include, but are not limited to, methyl, ethyl, propyl, isopropyl, butyl, isobutyl, tert-butyl, and the like. Optionally the alkyl group may be a substituted alkyl. In embodiments, the alkyl group may be a perhalo alkyl having a halogen such as, for example, fluorine, chlorine, bromine or iodine. In one embodiment, R₁ is a trifluoromethyl.

Suitable alkoxy groups as one or each of R₁ or R₂ include, but are not limited to, methoxy, ethoxy, propoxy, isopropoxy, butoxy, isobutoxy, tert-butoxy, and the like. In embodiments, R₁ and/or R₃ are independently selected from methoxy, ethoxy, and tert-butoxy.

When R₁ or R₃ is an aryl group, suitable aryls include aryl groups having about 6 to about 30 carbon atoms. The aryl group may optionally be a substituted aryl. The aryl group may optionally be substituted one, two, or more times by a substituent selected from the group consisting of an alkyl group having, for example, 1 to about 6 carbon atoms, an alkoxy group having, for example, 1 to about 6 carbon atoms, a dialkylamino group having, for example, 1 to about 3 carbon atoms, an aryl group having, for example, about 6 to about 30 carbon atoms, a substituted aryl, a halogen, a cyano group, and the like. Examples of suitable aryl groups for R₁ and/or R₃ include, but are not limited to, phenyl, naphthyl, methyl phenyl, tert-butyl phenyl, methoxy phenyl, ethoxy phenyl, butoxy phenyl, tert-butoxy phenyl, 3,5 diphenyl phenyl, 3,5-bis(p-tert-butyl phenyl)phenyl, and the like.

Heteroaryl groups suitable as R₁ and/or R₃ include heteroaryl groups of about 5 to about 24 carbon atoms, carbon atoms necessary to complete a fused heteroaromatic ring of furyl, thienyl, pyridyl, quinolynyl, and other heterocyclic systems. The hetero atom may be, for example, nitrogen, sulfur, or oxygen. The heteroaryl may optionally be substituted one, two, or more times by the same or a different moiety including, but not limited to, an alkyl having 1 to about 10 carbon atoms, an alkoxy having 1 to about 10 carbon atoms, a halogen such as fluorine, chlorine, and bromine, a cyano group, and the like.

It will be appreciated that an R group in a compound of Formula I may be a moiety or substituent different from other similarly designated R groups. For example, the R₃ groups on the respective anthracene rings of the material of Formula I may be the same or different moieties. This applies for each of the R₁ and R₂ groups on the material of Formula I.

Non-limiting examples of materials suitable as the fluorescent hydrocarbon component include, but are not limited to, the following compounds:

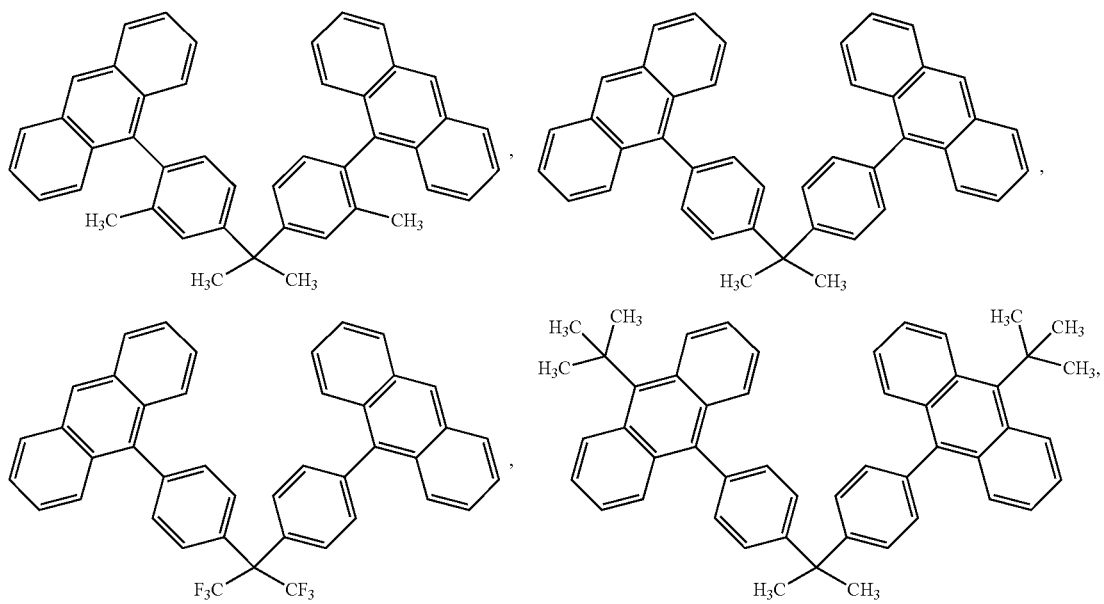

-continued
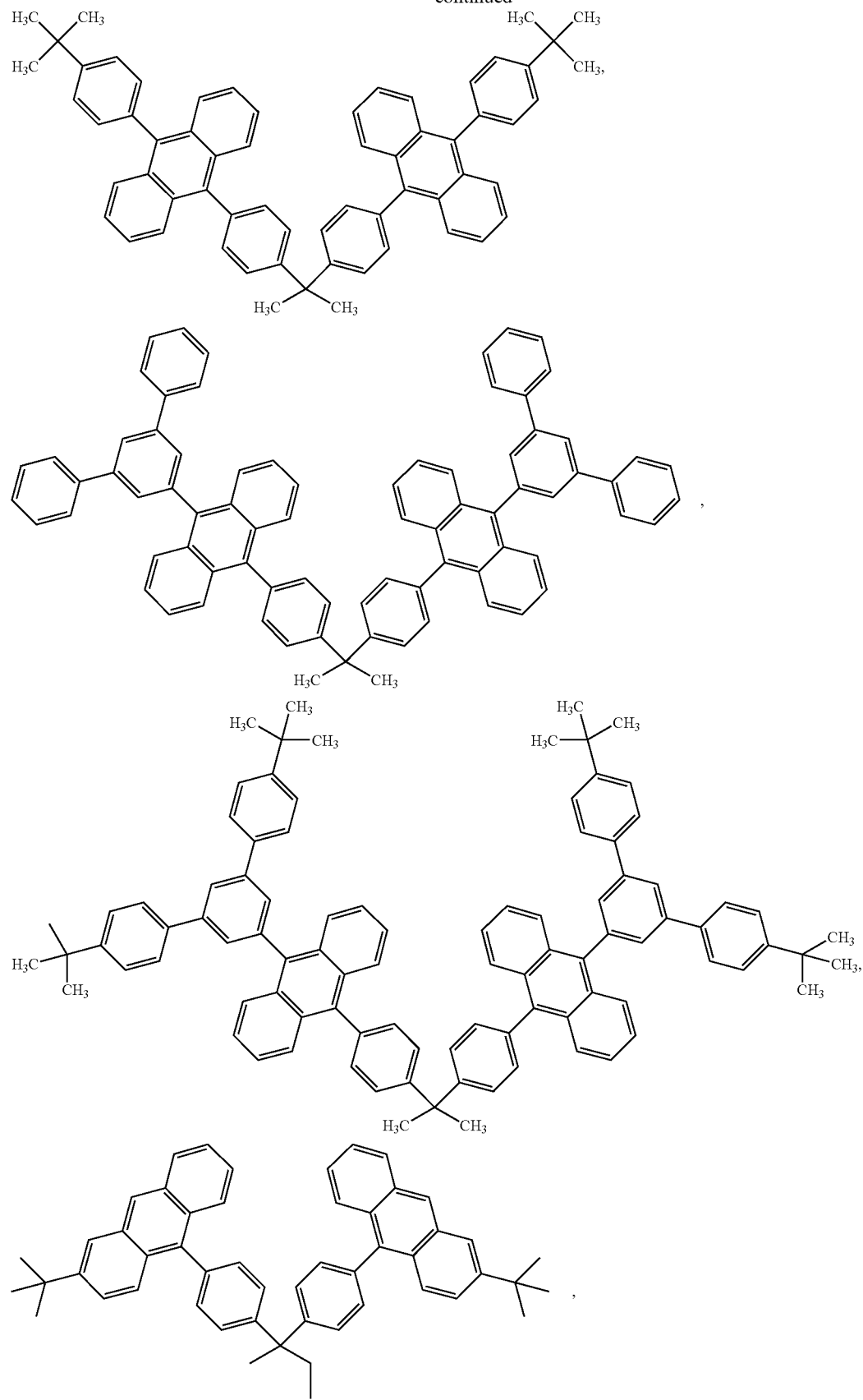

-continued

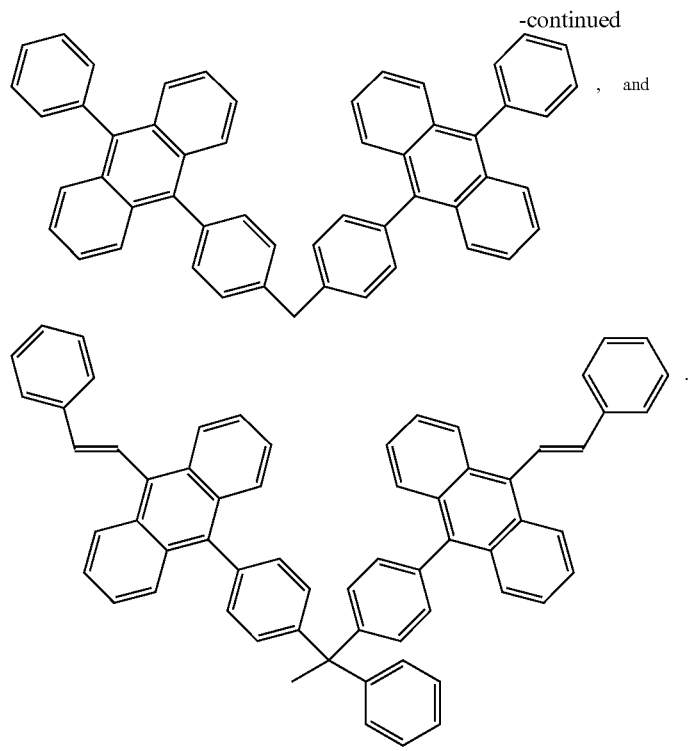, and

Figure 5:
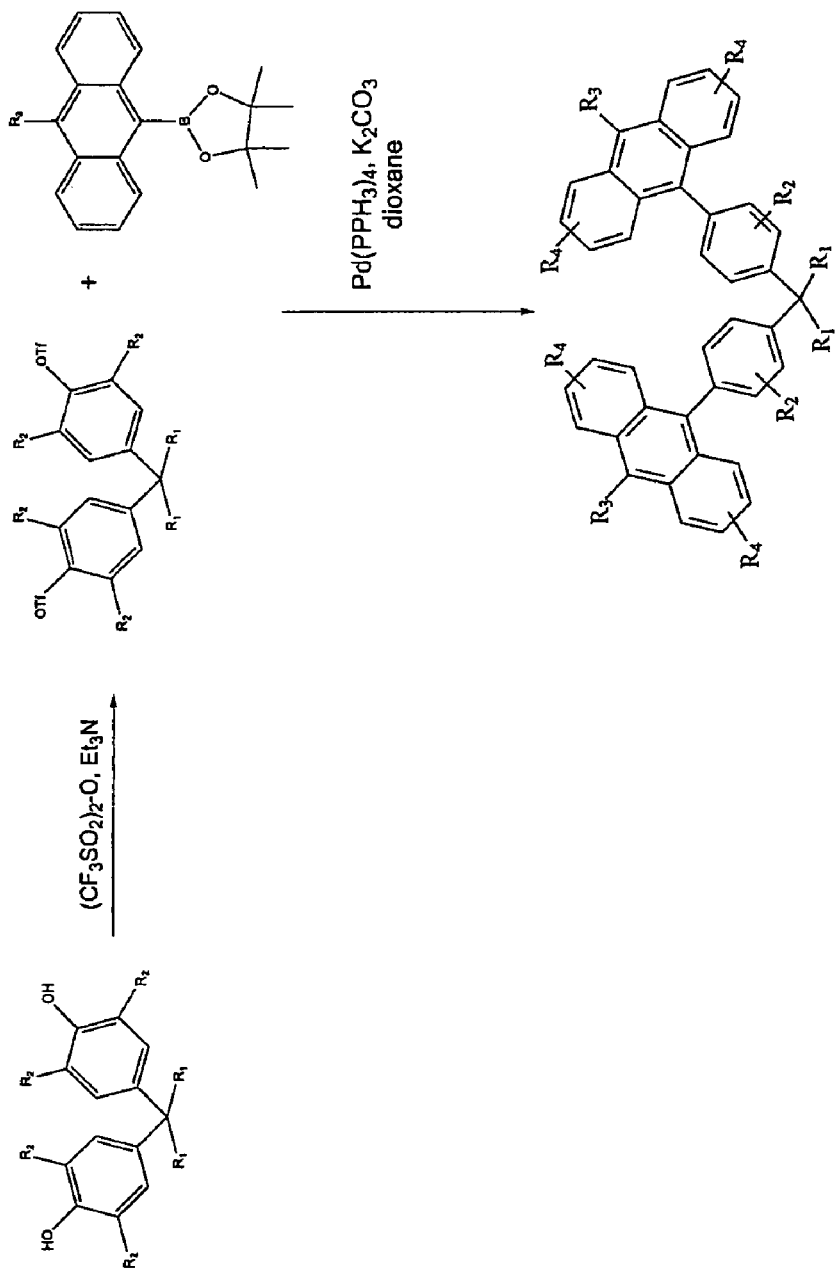
FIG. 5 is a schematic depicting the synthesis of a light-emitting material according to the present disclosure.

The fluorescent hydrocarbon materials according to the present disclosure may be synthesized by any conventional method including, for example, by utilizing the Suzuki reaction. With reference to FIG. 5, a synthesis route for preparing a fluorescent hydrocarbon material of the general Formula I is depicted. The synthesis comprises converting a bisphenol to its triflate analog. The triflate analog is then coupled with an appropriate boronic acid comprising a suitable anthracene derivative to produce the desired fluorescent hydrocarbon material. For example, they can be synthesized as follows: a mixture consisting of one equivalent of a suitable spiro-biphenyl triflate compound, such as 2,2'-bis(4-triflluoromethanesulfonatophenyl)propane, two equivalents of a base, such as potassium carbonate, two equivalents of an arene diborate compound such as 9-anthryl-4,4,5,5-tetramethyl-1,3,2-dioxaborolane, 0.01 equivalents of a palladium catalyst, such as tetrakis(triphenylphosphine)palladium, and suitable amounts of an inert solvent, such as dioxane, is heated under argon to reflux for a suitable time, about 48 hours. After cooling to room temperature, about 23° C., the reaction contents are added into methanol or water, and the precipitate is collected by filtration. The product may further be purified by standard purification means including recrystallization and sublimation. The compounds thus obtained may be confirmed by elemental analysis, NMR or IR spectrometric identification techniques.

The luminescent hydrocarbon materials described herein exhibit strong fluorescence in the solid state in the region from about 400 nanometers to, for example, about 600 nanometers. The have the ability of forming thin films with excellent thermal stability by vacuum evaporation.

The layers of an OLED comprising the present light-emitting materials may be transparent or opaque depending on the side of the OLED that is facing the viewer. Illustrative materials for the various potential layers of an OLED will now be discussed in constructing OLEDs in according with the present disclosure.

Materials suitable for the optional substrate include, for example, polymeric components, glass, quartz and the like. Suitable polymeric components include, but are not limited to polyesters such as MYLAR®, polycarbonates, polyacrylates, polymethacrylates, polysulfones, and the like. Other substrate materials can also be selected provided, for example, that the materials can effectively support the other layers, and do not interfere with the device functional performance.

In an embodiment, the substrate may be opaque. An opaque substrate can comprise various suitable materials including, for example, polymeric components like polyesters such as MYLAR®, polycarbonates, polyacrylates, polymethacrylates, polysulfones, and the like, which contain coloring agents or dyes such as carbon black. The substrate can also be comprised of silicon such as amorphous silicon, polycrystalline silicon, single crystal silicon, and the like. Another class of materials that can be used in the substrate are ceramics such as metallic compounds like metal oxides, halides, hydroxides, sulfides and others.

The substrate may have a thickness ranging, in embodiments, from about 10 to about 5,000 micrometers. In other embodiments, the substrate may have a thickness of from about 25 to about 1,000 micrometers.

An anode can comprise suitable positive charge injecting materials such as indium tin oxide (ITO), silicon, tin oxide, and metals with a work function ranging from about 4 eV to about 6 eV such as gold, platinum, and palladium. Other suitable materials for the anode include, but are not limited to, electrically conductive carbon, π-conjugated polymers such as polyaniline, polythiophene, polypyrrole, and the like having, for example, a work function equal to, or greater than, about 4 eV and, in embodiments, a work function of 4 eV to about 6 eV. A substantially transparent anode can comprise, for example, indium tin oxide (ITO), very thin substantially transparent metallic layers, comprising a metal with a work function ranging from about 4 eV to about 6 eV such as gold, palladium and the like, having a thickness, for example, from about 10 Å to about 200 Å, and, particularly, from about 30 Å to about 100 Å. Additional suitable forms of the anode are disclosed in U.S. Pat. Nos. 4,885,211 and 5,703,436, which are incorporated herein by reference in their entirety. An anode can also comprise a metal-organic mixed layer (MOML) as disclosed in U.S. patent application Ser. No. 10/117,812, which is published as U.S. Patent Application Publication No. 2002/0180349 and is incorporated herein by reference in its entirety. The thickness of the anode can range from about 10 Å to about 50,000 Å, with the preferred range depending on the electrical and optical constants of the anode material. One illustrative range of anode thickness is from about 300 Å to about 3,000 Å. Of course, a thickness outside of this range can also be used.

A cathode can comprise suitable electron injecting materials, such as metals, including high work function components, such as metals with, for example, a work function from about 4 eV to about 6 eV, or low work function components, such as metals with, for example, a work function of from about 2 eV to about 4 eV. The cathode can comprise a combination of a low work function (less than about 4 eV) metal and at least one other metal. Effective proportions of the low work function metal to the second or other metal are from less than about 0.1 weight percent to about 99.9 weight percent. Illustrative examples of low work function metals include, but are not limited to, alkaline metals such as lithium or sodium; Group 2A or alkaline earth metals such as beryllium, magnesium, calcium or barium; and Group III metals including rare earth metals and the actinide group metals such as scandium, yttrium, lanthanum, cerium, europium, terbium or actinium. Lithium, magnesium and calcium are preferred low work function metals. Exemplary cathode materials include the Mg—Ag alloy cathodes described in U.S. Pat. No. 4,885,211; U.S. Pat. No. 4,720,432; and, U.S. Pat. No. 5,703,436, the disclosures of which are totally incorporated herein by reference. Cathodes may also comprise a metal-organic mixed later (MOML) as disclosed in U.S. patent application Ser. No. 10/117,812, which is incorporated herein by reference in its entirety, and in U.S. Pat. No. 5,429,884, the disclosure of which is totally incorporated herein by reference. The cathodes can also be formed from lithium alloys with other high work function metals such as aluminum and indium.

A substantially transparent cathode can comprise very thin substantially transparent metallic layers comprising a metal with a work function ranging from about 2 eV to about 4 eV, such as, for example, Mg, Ag, Al, Ca, In, Li and their alloys. Examples of suitable metals include Mg:Ag alloys, comprised of, for example, from about 80 to 95 volume percent of Mg and about 20 to about 5 volume percent of Ag, and Li:Al alloys, comprised of, for example, from about 90 to 99 volume percent of Al, and from about 10 to about 1 volume percent of Li, and the like, having a thickness, for example, from about 10 Å to about 200 Å, and, particularly, from about 30 Å to about 100 Å. Of course, a thickness outside of this range can also be used.

The thickness of the cathode can range, in embodiments, from, for example, about 10 nanometers to about 1,000 nanometers. Thicknesses outside of this range can also be used.

The anode and cathode used in the present OLEDs each may be a single layer or may comprise two, three or more layers. For instance, the electrode may be composed of a charge injection layer (i.e., an electron injection layer or a hole injection layer) and a capping layer. In embodiments, however, the charge injection layer may be considered distinct from the electrode.

An electron injecting layer of the anode and/or cathode can include very thin substantially transparent metallic layers, composed of a metal with a work function ranging from about 2 eV to about 4 eV, such as Mg, Ag, Al, Ca, In, Li and their alloys such as Mg:Ag alloys composed of, for example, from about 80 to 95 volume percent of Mg and about 20 to about 5 volume percent of Ag, and Li:Al alloys, composed of, for example, from about 90 to 99 volume percent of Al, and from about 10 to about 1 volume percent of Li, and the like, having a thickness, for example, from about 10 Å to about 200 Å, and, particularly, from about 30 Å to about 100 Å. Of course, a thickness outside of these ranges can also be used. The electron injection layer can also include very thin insulative materials such as an oxide material or an alkaline metal compound as described in U.S. Pat. Nos. 5,457,565; 5,608,287 and 5,739,635, which are each incorporated herein by reference in their entirety.

A hole injecting layer of the anode and/or cathode can be composed of suitable positive charge injecting materials such as indium tin oxide (ITO), silicon, tin oxide, and metals with a work function ranging from about 4 eV to about 6 eV, such as, gold, platinum, and palladium. Other suitable materials for the hole injecting layer include, but are not limited to, electrically conductive carbon, π-conjugated polymers such as polyaniline, polythiophene, polypyrrole, and the like having, for example, a work function equal to, or greater than, about 4 eV, and particularly from about 4 eV to about 6 eV. A substantially transparent hole injecting material can be composed of very thin substantially transparent metallic layers, comprising a metal with a work function ranging from about 4 eV to about 6 eV, such as gold, palladium and the like, having a thickness, for example, from about 10 Å to about 200 Å, and, particularly, from about 30 Å to about 100 Å. Of course, a thickness outside of these ranges can also be used. Additional suitable forms of hole injecting layers are disclosed in U.S. Pat. Nos. 4,885,211 and 5,703,436, which are incorporated herein by reference in their entirety.

A capping layer on the anode and/or cathode can be included in order to increase the thermal stability, increase the environmental stability, and/or in some other way improve the performance of the organic light emitting device. An example of a capping layer that can be used to increase the thermal stability of the organic light emitting is a layer comprised of SiO, $SiO_2$, or mixtures thereof. Other examples are disclosed in U.S. Pat. Nos. 6,614,175 and 6,765,348, the disclosures of which are totally incorporated herein by reference. An example of a capping layer that can be used to increase the environmental stability of the organic light emitting device is a layer comprised of a stable metal such as Ag, Al, In, or Au. Another example of a capping layer that can be used to increase the environmental stability of the organic light emitting device is a layer comprised of a low work function metal as described for example in U.S. Pat. No. 5,059,861, the entire disclosure of which is incorporated herein by reference. The thickness of the capping layer can, for example, range from about 20 nanometers to about 5,000 nanometers. Typically, the thickness is from about 50 nanometers to 500 nanometers.

A buffer layer can be composed of a material with certain hole injection and transport properties and selected such that device performance is improved. Suitable materials that can be utilized in the buffer layer include semiconductive organic materials; such as, for example, porphyrin derivatives like 1,10,15,20-tetraphenyl-21H,23H-porphyrin copper (II) disclosed in U.S. Pat. No. 4,356,429, incorporated herein by reference in its entirety; copper phthalocyanine, copper tetramethyl phthalocyanine; zinc phthalocyanine; titanium oxide phthalocyanine; magnesium phthalocyanine; and the like, and wherein copper phthalocyanine is one preferred example. Mixtures of these and other suitable materials can also be used. Other suitable materials that can be utilized in the buffer layer include semiconductive and insulative metal compounds, such as for example metal oxides like MgO, $Al_2O_3$, BeO, BaO, AgO, SrO, SiO, $SiO_2$, $ZrO_2$, CaO, $Cs_2O$, $Rb_2O$, $Li_2O$, $K_2O$ and $Na_2O$; and metal halides, like LiF, KCl, NaCl, CsCl, CsF and KF. The buffer layer can have a thickness ranging from about 1 nm to about 100 nm. An illustrative thickness range for the buffer layer is from about 5 nm to about 25 nm. Another illustrative thickness range for the buffer layer is from about 1 nm to about 5 nm.

A class of hole transporting materials that can be selected for the buffer layer are the aromatic tertiary amines, such as those disclosed in U.S. Pat. No. 4,539,507, the disclosure of which is totally incorporated herein by reference. Representative examples of aromatic tertiary amines are bis(4-dimethylamino-2-methylphenyl)phenylmethane; N,N,N-tri(p-tolyl)amine; 1,1-bis(4-di-p-tolylaminophenyl)cyclohexane; 1,1-bis(4-di-p-tolylaminophenyl)-4-phenyl cyclohexane; N,N'-diphenyl-N,N'-bis(3-methylphenyl)-1,1'-biphenyl-4,4'-diamine; N,N'-diphenyl-N,N'-bis(3-methylphenyl)-1,1'-biphenyl-4,4'-diamine; N,N'-diphenyl-N,N'-bis(4-methoxyphenyl)-1,1'-biphenyl-4,4'-diamine; N,N,N',N'-tetra-p-tolyl-1,1'-biphenyl-4,4'-diamine; N,N'-di-1-naphthyl-N,N'-diphenyl-1,1'-biphenyl-4,4'-diamine; and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluid ine; N,N-bis-[4'-(N-phenyl-N-p-tolylamino)4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)4-biphenylyl]-m-toluidine; N,N-bis-[4'-(N-phenyl-N-m-chlorophenylamino)-4-biphenylyl]-m-toluidine; N,N-bis-[4'-(N-phenyl-N-'-m-chlorophenylamino)4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene and the like.

A buffer layer comprised of one or more aromatic tertiary amines described above may further include, as disclosed in U.S. Pat. No. 5,846,666, the disclosure of which is totally incorporated herein by reference, a stabilizer comprised of certain hydrocarbon compounds, such as rubrene, 4,8-diphenylanthracene, and the like. The buffer layer can be prepared by forming a suitable compound into a thin film by known methods, such as vapor deposition or spin-coating. The thickness of buffer layer thus formed is not particularly limited, and can be in a range of, for example, from about 5 nanometers to about 300 nanometers, and, in some embodiments, from about 10 nanometers to about 100 nanometers.

The luminescent region, particularly the light emitting zone, can further include from about 0.01 weight percent to about 25 weight percent (based on the weight of the light emitting zone) of a luminescent material as a dopant. Examples of dopant materials that can be utilized in the luminescent region are fluorescent materials, such as coumarin, dicyanomethylene pyranes, polymethine, oxabenzanthrane, xanthene, pyrylium, carbostyl, perylene, and the like. Another preferred class of fluorescent materials are quinacridone dyes. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylq-uinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone, and the like as disclosed in U.S. Pat. Nos. 5,227,252; 5,276,381 and 5,593,788, each incorporated herein by reference in its entirety. Another class of fluorescent materials that may be used is fused ring fluorescent dyes. Exemplary suitable fused ring fluorescent dyes include perylene, rubrene, anthracene, coronene, phenanthrecene, pyrene and the like, as disclosed in U.S. Pat. No. 3,172,862, which is incorporated herein by reference in its entirety. Also, fluorescent materials include butadienes, such as 1,4-diphenylbutadiene and tetraphenylbutadiene, and stilbenes, and the like, as disclosed in U.S. Pat. Nos. 4,356,429 and 5,516,577, each incorporated herein by reference in its entirety. Other examples of fluorescent materials that can be used are those disclosed in U.S. Pat. No. 5,601,903, which is incorporated herein by reference in its entirety.

Additionally, luminescent dopants that can be utilized in the luminescent region are the fluorescent dyes disclosed in U.S. Pat. No. 5,935,720, which is incorporated herein by reference in its entirety, such as 4-(dicyanomethylene)-2-l-propyl-6-(1,1,7,7-tetramethyljulolidyl-9-enyl)-4H-pyran (DCJTB); the lanthanide metal chelate complexes, such as for example, tris(acety lacetonato)(phenanthroline)terbium, tris (acetyl acetonato)(phenanthroline)europium, and tris (thenoyl trisfluoroacetonato)(phenanthroline)europium, and those disclosed in Kido et al., "White light emitting organic electroluminescent device using lanthanide complexes," *Jpn. J. Appl. Phys.*, Volume 35, pp. L394-L396 (1996), which is incorporated herein by reference in its entirety; and phosphorescent materials, such as organometallic compounds containing heavy metal atoms that lead to strong spin-orbit coupling, such as those disclosed in Baldo et al., "Highly efficient organic phosphorescent emission from organic electroluminescent devices," *Letters to Nature*, Volume 395, pp. 151-154 (1998), which is incorporated herein by reference in its entirety. Suitable examples of such materials include 2,3,7,8, 12,13,17,18-octaethyl-21H23H-phorpine platinum(II) (PtOEP) and fac tris(2-phenylpyridine)iridium ($Ir(ppy)_3$).

The luminescent region, and in particular the hole transport zone, can also include one or more other materials with hole transporting properties. Examples of hole-transporting materials that can be utilized in the luminescent region include polypyrrole, polyaniline, poly(phenylene vinylene), polythiophene, polyarylamine as disclosed in U.S. Pat. No. 5,728, 801, which is incorporated herein by reference in its entirety, and their derivatives, and known semiconductive organic materials; porphyrin derivatives such as 1,10,15,20-tetraphenyl-21H,23H-porphyrin copper (II) disclosed in U.S. Pat. No. 4,356,429, incorporated herein by reference in its entirety; copper phthalocyanine, copper tetramethyl phthalocyanine; zinc phthalocyanine; titanium oxide phthalocyanine; magnesium phthalocyanine; and the like.

A specific class of hole transporting materials that can be utilized in the luminescent region are the aromatic tertiary amines such as those disclosed in U.S. Pat. No. 4,539,507, which is incorporated herein by reference in its entirety. Suitable exemplary aromatic tertiary amines include, but are not limited to, bis(4-dimethylamino-2-methylphenyl)phenylmethane; N,N,N-tri(p-tolyl)amine, 1,1-bis(4-di-p-tolylaminophenyl)cyclohexane; 1,1-bis(4-di-p-tolylaminophenyl)-4-phenyl cyclohexane; N,N'-diphenyl-N,N'-bis(3-methylphenyl)-1,1'-biphenyl-4,4'-diamine; N,N'-diphenyl-N,N'-bis(3-methylphenyl)-1,1'-biphenyl-4,4'-diamine; N,N'-diphenyl-N,N'-bis(4-methoxyphenyl)-1,1'-biphenyl-4,4'-diamine; N,N,N',N'-tetra-p-tolyl-1,1'-biphenyl-4,4'-diamine; N,N'-di-1-naphthyl-N,N'-diphenyl-1,1'-biphenyl-4,4'-diamine; N,N'-bis(p-biphenyl)-N,N'-diphenyl benzidine(biphenyl TPD); mixtures thereof and the like. A preferred class of tertiary aromatic amines that can be used in the luminescent region are the naphtyl-substituted benzidine derivatives, such as, N,N'-di(naphthalene-1-yl)-N,N'-diphenyl-benzidine (NPB). Another class of aromatic tertiary amines are polynuclear aromatic amines. Examples of these polynuclear aromatic amines include, but are not limited to, N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-tolu id ine; N,N-bis-[4'-(N-phenyl-N-p-chlorophenylamino)-4-biphenylyl]-m-toluidine; N,N-bis-[4'-(N-phenyl-N-m-chlorophenylamino)4-biphenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene, mixtures thereof and the like; 4,4'-bis(9-carbazolyl)-1,1'-biphenyl compounds, such as 4,4'-bis(9-carbazolyl)-1,1'-biphenyl and 4,4'-bis(3-methyl-9-carbazolyl)-1,1'-biphenyl, and the like.

A specific class of the hole transporting materials that can be used in the luminescent region are the indolo-carabazoles, such as those disclosed in U.S. Pat. Nos. 5,942,340 and 5,952,115, each incorporated herein by reference in its entirety, such as 5,11-di-naphthyl-5,11-dihydroindolo[3,2-b]carbazole, and 2,8-dimethyl-5,11-di-naphthyl-5,11-dihydroindolo[3,2-b]carbazole; N,N,N'N'-tetraarylbenzidines, wherein aryl may be selected from phenyl, m-tolyl, p-tolyl, m-methoxyphenyl, p-methoxyphenyl, 1-naphthyl, 2-naphthyl and the like. Illustrative examples of N,N,N'N'-tetraarylbenzidine are N,N-di-1-naphthyl-N,N'-diphenyl-1,1'-biphenyl-4,4'-diamine; N,N'-bis(3-methylphenyl)-N,N'-diphenyl-1,1'-biphenyl-4,4'-diamine; N,N'-bis(3-methoxyphenyl)-N,N'-diphenyl-1,1'-biphenyl-4,4'-diamine, and the like.

The optional electron transporting layer selected for the primary purpose of improving the electron injection characteristics and the emission uniformity of electroluminescent devices in accordance with the present disclosure are of a suitable thickness, for example from about 1 nanometer to about 300 nanometers, or from about 5 nanometers to about 100 nanometers. Illustrative examples of electron transporting compounds, which can be utilized in this layer, include the metal chelates of 8-hydroxyquinoline as disclosed in U.S. Pat. Nos. 4,539,507; 5,151,629, and 5,150,006, the disclosures of which are totally incorporated herein by reference. Illustrative examples include tris(8-hydroxyquinolinate)aluminum; tris(8-hydroxyquinolinate)gallium; bis(8-hydroxyquinolinate)magnesium; bis(8-hydroxyquinolinate)zinc; tris(5-methyl-8-hydroxyquinolinate)aluminum; tris(7-propyl-8-quinolinolato)aluminum; bis[benzo{f}-8-quinolinolato]zinc; bis(10-hydroxybenzo[h]quinolinate)beryllium; and the like. Another class of metal chelate compounds suitable for the electron transport layer is the oxadiazole metal chelates disclosed in U.S. Pat. No. 5,925,472, the entire disclosure of which is incorporated herein by reference.

Another class of suitable electron transport materials comprises triazine compounds as disclosed in U.S. Pat. Nos. 6,057,048; 6,225,467; and 6,229,012, the disclosures of which are totally incorporated herein by reference. Illustrative specific examples include 4,4'-bis-[2-(4,6-diphenyl-1,3,5-triazinyl)]-1,1'-biphenyl; 4,4'-bis-[2-(4,6-d]-p-tolyl-1,3,5-triazinyl)]-1,1'-biphenyl; 4,4'-bis-[2-(4,6-di-m-tolyl-1,3,5-triazinyl)]-1,1'-biphenyl; 4,4'-bis-[2-(4,6-di-p-anisyl-1,3,5-triazinyl)]-1,1'-biphenyl; 4,4'-bis-[2-(4-p-naphthyl-6-phenyl-1,3,5-triazinyl)]-1,1'-biphenyl; 4,4'-bis-[2-(4,6-di-biphenylyl-1,3,5-triazinyl)]-1,1'-biphenyl; 4,4'-bis-[2-(4,6-diphenyl-1,3,5-triazinyl)]-2,2'-dimethyl-1,1'-biphenyl; 4,4'-bis-[2-(4,6-di-phenyl-1,3,5-triazinyl)]-stilbene; 4,4'-bis-[2-(4-phenyl-6-p-tolyl-1,3,5-triazinyl)]-stilbene; 2,4,6-tri(4-biphenylyl)-1,3,5-triazine; and the like.

In embodiments, the luminescent region can include one or more non-anthracene and non-triazine derivative compounds which have the desired properties such as electron transporting and/or light emitting properties. In embodiments, a number of the following exemplary non-anthracene and non-triazine derivative compounds may have electron transporting and/or light emitting properties and thus may be useful in the luminescent region (in for example the light emitting zone and/or the electron transport zone): polyfluorenes, such as poly(9,9-di-n-octylfluorene-2,7-diyl), poly(2,8-(6,7,12,12-tetraalkylindenofluorene) and copolymers containing fluorenes such as fluorene-amine copolymers, as disclosed in incorporated Bernius et al., Proceedings of SPIE Conference on Organic Light Emitting Materials and Devices III, Denver, Colo., July 1999, Volume 3797, p. 129.

Other suitable non-anthracene and non-triazine derivative compounds may include metal oxinoids as disclosed in U.S. Pat. Nos. 4,539,507; 5,151,629; 5,150,006; 5,141,671; and 5,846,666, the entire disclosures of which are incorporated herein by reference. Illustrative specific examples include tris(8-hydroxyquinolinate)aluminum ($Alq_3$), and bis(8-hydroxyquinolato)-(4-phenylphenolato)aluminum (BAlq). Other examples include tris(8-hydroxyquinolinate)gallium; bis(8-hydroxyquinolinate)magnesium; bis(8-hydroxyquinolinate)zinc; tris(5-methyl-8-hydroxyquinolinate)aluminum; tris(7-propyl-8-quinolinolato)aluminum; bis[benzo{f}-8-quinolinate]zinc; bis(10-hydroxybenzo[h]quinolinate)beryllium; and the like.

Another suitable class of non-anthracene and non-triazine derivative compounds is stilbene derivatives, such as those disclosed in U.S. Pat. No. 5,516,577, the disclosure of which is totally incorporated herein by reference. Further examples of non-anthracene and non-triazine derivative compounds are the metal thioxinoid compounds, illustrated in U.S. Pat. No. 5,846,666, the disclosure of which is totally incorporated herein by reference, such as metal thioxinoid compounds of bis(8-quinolinethiolato)zinc; bis(8-quinolinethiolato)cadmium; tris(8-quinolinethiolato)gallium; tris(8-quinolinethiolato)indium; bis(5-methylquinolinethiolato)zinc; tris(5-methylquinolinethiolato)gallium; tris(5-methylquinolinethiolato)indium; bis(5-methylquinolinethiolato)cadmium; bis(3-methylquinolinethiolato)cadmium; bis(5-methylquinolinethiolato)zinc; bis[benzo{f}-8-quinolinethiolato]zinc; bis[3-methylbenzo{f}-8-quinolinethiolato]zinc; bis[3,7-dimethylbenzo{f}-8-quinolinethiolato]zinc; and the like. Specific non-anthracene and non-triazine derivative compounds are bis(8-quinolinethiolato)zinc; bis(8-quinolinethiolato)cadmium; tris(8-quinolinethiolato)gallium; tris(8-quinolinethiolato)indium and bis[benzo{f}-8-quinolinethiolato]zinc. Other suitable non-anthracene and non-triazine derivative compounds are the oxadiazole metal chelates disclosed in incorporated U.S. Pat. No. 5,925,472, which materials include bis[2-(2-hydroxyphenyl)-5-phenyl-1,3,4-oxadiazolato]zinc; bis[2-(2-hydroxyphenyl)-5-phenyl-1,3,4-oxadiazolato]beryllium; bis[2-(2-hydroxyphenyl)-5-(1-naphthyl)-1,3,4-oxadiazolato]zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis(2-hydroxyphenyl)-5-phenyl-1,3,4-oxadiazolato]lithium; bis[2-(2-hydroxyphenyl)-5-p-tolyl-1,3,4-oxadiazolato]zinc; bis[2-(2-hydroxyphenyl)-5-p-tolyl-1,3,4-oxadiazolato]beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato]zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato]zinc; bis[2-(2-hydroxyphenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-α-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis[2-(2-hydroxyphenyl)-5-p-pyridyl-1,3,4-oxadiazolato]beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato]beryllium, and the like. Another suitable class of non-anthracene and non-triazine derivative compounds are the quinolines, such as, for example, 1,4-bis(4-phenylquinolin-2-yl)benzene, 4,4'-bis(4-phenylquinolin-2-yl)-1,1'-biphenyl (TA).

In embodiments where the luminescent region includes one or more hole transport material and/or one or more electron transport material in addition to the organic electroluminescent material(s), the organic electroluminescent material, the hole transport material(s), and/or the electron transport material(s) can be formed in separate layers, such as the OLEDs disclosed in U.S. Pat. Nos. 4,539,507; 4,720,432 and 4,769,292; or in the same layer thus forming mixed areas of two or more materials, such as the OLEDs disclosed in U.S. Pat. Nos. 5,853,905; 5,925,980; 6,130,001, 6,114,055; 6,392,250; 6,392,339; and 6,614,175. The disclosures of these patents and patent applications are incorporated herein by reference in their entirety.

The thickness of the luminescent region can vary for example, from about 10 Å to about 10,000 Å, typically from about 200 Å to about 2,000 Å, and particularly from about 500 Å to about 1,500 Å. In embodiments wherein the luminescent region includes two or more layers, the thickness of each layer can, for example, be from about 10 Å to about 5,000 Å, typically from about 50 Å to about 2,000 Å, and particularly from about 100 Å to about 1,500 Å.

Each layer of the OLED may have a generally uniform or non-uniform composition across the layer thickness where each layer is composed entirely of one material or a mixture of materials.

It will be appreciated that a display device in accordance with the present disclosure may also include one or more light-absorbing layers in any of the cathode, anode, and luminescent regions, or outside of the anode or cathode. Examples of suitable light-absorbing layers including, but not limited to, layers comprising metal-organic mixed layers as described in, for example, U.S. Patent Application Publication Nos. 2002/0180349 and 2003/0234609, the entire disclosures of which are incorporated herein by reference, and the light-absorbing layers of copending application [20031599-US-NP], the entire disclosure of which is incorporated herein by reference.

The OLED can be fabricated by sequentially forming the desired layers on the substrate using any suitable thin film forming technique, typically, spin coating or deposition by thermal evaporation in vacuum. More details about fabrication and operation of organic light emitting devices are disclosed, for example, in U.S. Pat. Nos. 4,539,507; 4,769,292; 6,392,339; 6,392,250; and 6,614,175, the disclosure of each patent and patent application being totally incorporated herein by reference.

An organic light emitting device in accordance with the present disclosure can demonstrate an improved performance, such as, a higher operational stability and improved color purity, compared to other light emitting devices, such as, for example, OLEDs.

The invention will now be described in detail with respect to specific embodiments thereof, it being understood that these examples are intended to be illustrative only and the invention is not intended to be limited to the materials, conditions, or process parameters recited herein. All percentages and parts are by weight unless otherwise indicated.

EXAMPLE I

Synthesis of
9-Anthryl-4,4,5,5-tetramethyl-1,3,2-dioxaborolane

To a solution of 9-bromoanthracene (9.73 grams) in 100 milliliters of anhydrous diethyl ether were slowly added at about 0° C. 23 milliliters of 2M n-butyllithium in hexane solution. After the addition, the reaction mixture was warmed to room temperature (about 23° C.) for 30 minutes. The resulting mixture was then cooled to around −30° C. and 2-isopropoxy-4,4,5,5-tetramethyl-1,3,3-dioxaborolane (9.27 milliliters) was added through a syringe. The resulting reaction mixture was warmed to room temperature (about 23° C.) and stirred overnight (about 18 hours throughout). After being diluted with 50 milliliters of hexane, the resulting mixture was filtered through celite. Removal of the solvents under reduced pressure yielded a yellowish solid (6.70 grams) which contains more than 90 percent of 9-anthryl-4,4,5,5-tetramethyl-1,3,2-dioxaborolane. The product may be used without further purification. This compound and its structure was confirmed by proton NMR analysis.

EXAMPLE II

Synthesis of 2,2'-bis(4-trifluoromethanesulfonato-3-methylphenyl)propane

To a solution of bisphenol C (10 grams, 39.01 mmol) in 100 milliliters of dichloromethane was added anhydrous triethylamine (11.42 mL, 81.92 mmol) at 0° C. (ice bath) under argon. The trifluoromethane sulfonic anhydride (13.84 mL, 81.92 mmol) was then added slowly. The reaction was allowed to stir overnight at room temperature. The reaction was quenched with saturated aqueous brine solution and the aqueous layer was then removed. The organic layer was washed with 5% aqueous HCl solution and then water. After removal of the solvents, the resulting crude residue was purified through a silica column to yield 15.28 grams of 2,2'-bis(4-trifluoromethanesulfonato-3-methylphenyl)propane. This compound and its structure was confirmed by proton NMR analysis.

EXAMPLE III

Synthesis of 2,2'-bis[4-(9-anthryl)-3-methyl phenyl]propane

A mixture of 9-anthryl-4,4,5,5-tetramethyl-1,3,2-dioxaborolane (7.74 grams, 25.45 mmol), 2,2'-bis(4-trifluoromethanesulfonato-3-methylphenyl)propane (5.0 grams, 12.12 mmol), potassium carbonate (3.68 grams, 26.66 mmol) in 50 milliliters of dioxane was purged with argon for 10 minutes. To this mixture was then added tetrakis(triphenylphosphine)palladium (0.56 grams, 0.485 mmol). The reaction mixture was stirred at reflux for 48 hours under argon. After cooling to room temperature (about 23° C.), the mixture was diluted with 50 milliliters of methanol, and the precipitates were collected by filtration, washed with 5 percent HCl aqueous solution, followed by water to remove inorganic salts. After drying, the filtrates were purified by sublimation to yield 3.97 grams of 2,2'-bis[4-(9-anthryl)-3-methylphenyl]propane. This compound had a melting point of 289° C. The structure of this compound was confirmed by proton NMR and elemental analysis.

EXAMPLE IV

Synthesis of 2,2'-bis(4-triflluoromethane-sulfonatophenyl)propane

To a solution of bisphenol A (10 grams, 43.80 mmol) in 100 milliliters of dichloromethane was added anhydrous triethylamine (12.82 mL, 91.99 mmol) at 0° C. (ice bath) under argon. The trifluoromethane sulfonic anhydride (15.53 mL, 91.99 mmol) was then added slowly. The reaction was allowed to stir overnight at room temperature. The reaction was quenched with saturated aqueous brine solution and the aqueous layer was then removed. The organic layer was washed with 5% aqueous HCl solution and then water. After removal of the solvents, the resulting crude residue was purified through a silica column to yield 15.21 grams of 2,2'-bis(4-trifluoromethanesulfonatophenyl)propane. This compound and its structure was confirmed by proton NMR analysis.

EXAMPLE V

Synthesis of 4,4'-bis[4-(9-anthryl)phenyl]propane

A mixture of 9-anthryl-4,4,5,5-tetramethyl-1,3,2-dioxaborolane (8.96 grams, 29.5 mmol), 2,2'-bis(4-trifluoromethanesulfonatophenyl)propane (5.39 grams, 14.03 mmol), potassium carbonate (4.26 grams, 30.9 mmol) in 75 milliliters of dioxane was purged with argon for 10 minutes. To this mixture was then added tetrakis(triphenylphosphine)palladium (1.3 grams, 1.12 mmol). The reaction mixture was stirred at reflux for 48 hours under argon. After cooling to room temperature (about 23° C.), the mixture was diluted with 50 milliliters of methanol, and the precipitates were collected by filtration, washed with 5 percent HCl aqueous solution, followed by water to remove inorganic salts. After drying, the filtrates were purified by sublimation to yield 4.88 grams of 4,4'-bis[4-(9-anthryl)phenyl]propane. This compound had a melting point of 245° C. The structure of this compound was confirmed by proton NMR and elemental analysis.

EXAMPLE VI

Synthesis of 2,2'-bis(4-triflluoromethane-sulfonatophenyl)hexafluoropropane

To a solution of bisphenol AF (10 grams, 43.80 mmol) in 100 milliliters of dichloromethane was added anhydrous triethylamine (12.82 mL, 91.99 mmol) at 0° C. (ice bath) under argon. The trifluoromethane sulfonic anhydride (15.53 mL, 91.99 mmol) was then added slowly. The reaction was allowed to stir overnight at room temperature. The reaction was quenched with saturated aqueous brine solution and the aqueous layer was then removed. The organic layer was washed with 5% aqueous HCl solution and then water. After removal of the solvents, the resulting crude residue was purified through a silica column to yield 15.46 grams of 2,2'-bis(4-trifluoromethanesulfonatophenyl)hexafluoropropane. This compound and its structure was confirmed by proton NMR analysis.

EXAMPLE VII

Synthesis of 4,4'-bis[4-(9-anthryl)phenyl]hexafluoropropane

A mixture of 9-anthryl-4,4,5,5-tetramethyl-1,3,2-dioxaborolane (5.00 grams, 16.42 mmol), 2,2'-bis(4-trifluoromethanesulfonatophenyl)hexafluoropropane (3.16 grams, 8.21 mmol), potassium carbonate (2.38 grams, 17.24 mmol) in 50 milliliters of dioxane was purged with argon for 10 minutes. To this mixture was then added tetrakis(triphenylphosphine)palladium (0.38 grams, 0.328 mmol). The reaction mixture was stirred at reflux for 48 hours under argon. After cooling to room temperature (about 23° C.), the mixture was diluted with 25 milliliters of methanol, and the precipitates were collected by filtration, washed with 5 percent HCl aqueous solution, followed by water to remove inorganic salts. After drying, the filtrates were purified by sublimation to yield 2 grams of 4,4'-bis[4-(9-anthryl)phenyl]hexafluoropropane. This compound had a melting point of 277° C. The structure of this compound was confirmed by proton NMR and elemental analysis.

EXAMPLES VIII-X

Separate organic electroluminescent devices comprising a light-emifting layer comprising a fluorescent hydrocarbon material of Examples III, V and VII were fabricated in the following manner;

A 500 Å indium tin oxide (ITO) anode coated glass substrate was selected, the thickness of the glass substrate being about 1 millimeter. The glass was cleaned with a commercial detergent, rinsed with deionized water and dried in a vacuum oven at 60° C. for 1 hour. Immediately before use, the glass was treated with UV ozone for 0.5 hour.

The ITO anode coated on the glass substrate was then placed in a vacuum deposition chamber, and a buffer layer was applied. The buffer layer deposition rate and layer thickness were controlled by an Inficon Model IC/5 controller. Under a pressure of about $5\times10^{-6}$ Torr, a 15 nanometers thick buffer layer was deposited on the ITO glass substrate through evaporation of copper (II) phthalocyanine at a rate of 0.6 nanometer/second from a tantalum boat.

Onto the buffer layer, a 20 nanometer thick hole transport layer of N,N'-1-naphthyl-N,N'-diphenyl-1,1'-biphenyl-4,4'-diamine was deposited at a rate of 0.6 nanometer/second.

Onto the hole transport layer was deposited by evaporation a 40 nanometer light emitting layer of one of the materials of Examples III, V and VII at a rate of 0.6 nanometer/second.

A 20 nanometers thick electron transport layer of 4,4'-bis-[2-(4,6-diphenyl-1,3,5-triazinyl)]-1,1'-biphenyl was then deposited by evaporation at a rate of 0.6 nanometer/second onto the light emitting layer.

A 100 nanometer cathode of a magnesium silver alloy or aluminum was deposited at a total deposition rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The electroluminescent device as prepared above were retained in a dry box which was continuously purged with nitrogen gas. Their performance was assessed by measuring the current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

The light output from the devices when driven by a direct current of 25 mA/cm$^2$ is displayed in Table 1. The devices emitted a blue emission. The CIE color coordinates as measured by Minolta Chromameter CS-100 are also displayed in Table 1.

TABLE 1

| Device | Light Emitting Material | Color Coordinates | Light Ouput (cd/m$^2$) |
|---|---|---|---|
| Example VIII | Example III | (0.165, 0.191) | 160 |
| Example IX | Example V | (0.183, 0.257) | 415 |
| Example X | Example VII | (0.194, 0.250) | 285 |

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, improvements and substantial equivalents thereof.

The invention claimed is:

1. An organic light-emitting device comprising an anode, a cathode, and an eluminescent region disposed between said anode and said cathode, said eluminescent comprising a light-emitting material of the formula

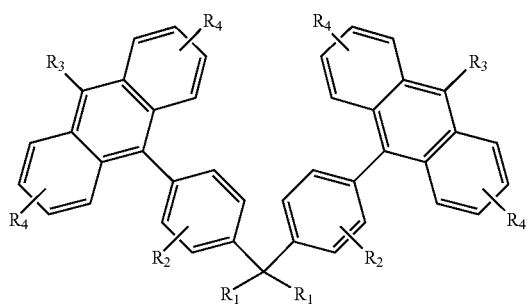

wherein $R_1$ is independently selected from the group consisting of an alkyl group, an aryl group, a heteroaryl group, an alkoxy group, an amino group, an alkyl amino group, and an aryl amino group; R2 is independently selected from the group consisting of hydrogen, and an alkyl group; $R_3$ is independently selected from the group consisting of hydrogen, an alkyl group, an alkoxy group, a halogen atom, and a cyano group; and, R4 is independently selected from the group consisting of hydrogen, an alkyl group, an aryl group, a heteroaryl group, an alkoxy group, a halogen atom, and a cyano group.

2. The organic light-emitting device according claim 1, wherein said light-emitting material is of the formula

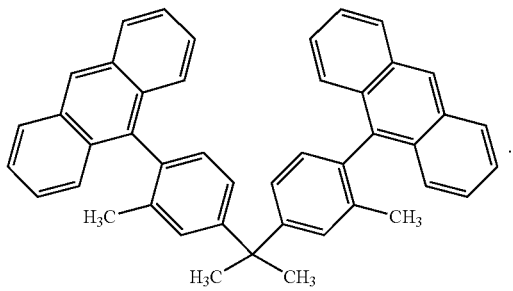

3. The organic light-emitting device according to claim 1, wherein said light-emitting material is of the formula

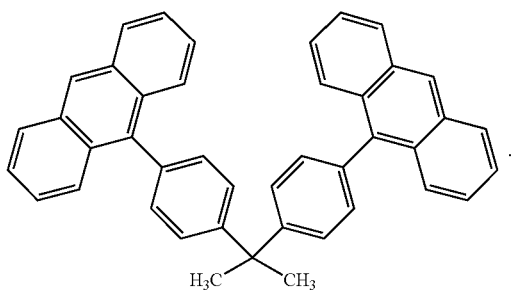

4. The organic light-emitting device according to claim 1, wherein said light-emitting material is of the formula

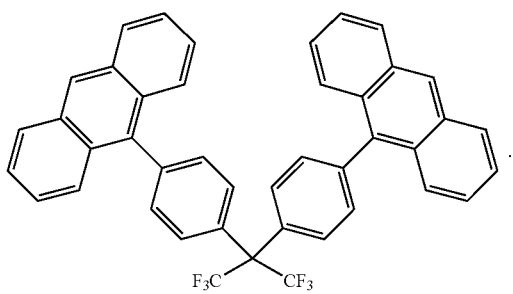

5. The organic light-emitting device according to claim 1, wherein $R_1$ is independently selected from the group consisting of alkyl group having 1 to 10 carbon atoms, an alkyl group having 1 to about 10 carbon atoms wherein at least one of said $R_1$ alkyl groups comprises one or more halogen atoms, an aryl group having about 6 to about 30 carbon atoms, a heretoaryl group having about 5 to about 24 carbon atoms, and an alkoxy group having 1 to about 24 carbon atoms; R2 is independently selected from the group consisting of hydrogen, and an alkyl group having 1 to about 10 carbon atoms; and $R_3$ is independently selected from the group consisting of hydrogen, an alkyl group having 1 to about 10 carbon atoms, an alkoxy group having 1 to about 24 carbon atoms, and a halogen.

6. The organic light-emitting device according to claim 1, wherein $R_1$ is an alkyl group having 1 to about 10 carbon atoms; $R_2$ is independently selected from the group consisting of hydrogen, and an alkyl group having 1 to about 10 carbon atoms; and $R_3$ is independently selected from the group consisting of hydrogen, and an alkyl group having 1 to about 10 carbon atoms.

7. The organic light-emitting device according to claim 1, wherein $R_1$ is independently selected from the group consisting of methyl, ethyl, propyl, isopropyl, butyl, isobutyl, tert-butyl, trifluoromethyl, methoxy, ethoxy, propoxy, isopropoxy, butoxy, isobutoxy, tert-butoxy, phenyl, and tert-butylphenyl; $R_2$ is independently selected from hydrogen, methyl, ethyl, propyl, and butyl; and $R_3$ is independently selected from the group consisting of hydrogen, methyl, ethyl, propyl, isopropyl, butyl, isobutyl, tert-butyl, methoxy, ethoxy, butoxy, and tert-butoxy.

8. A display device comprising:
a first electrode;
a second electrode; and
a luminescent region disposed between said first and said second electrode, said luminescent region comprising a first charge transport layer, light-emitting layer, and a second charge transport layer,
wherein said light-emitting layer comprises a light-emitting material of the Formula I:

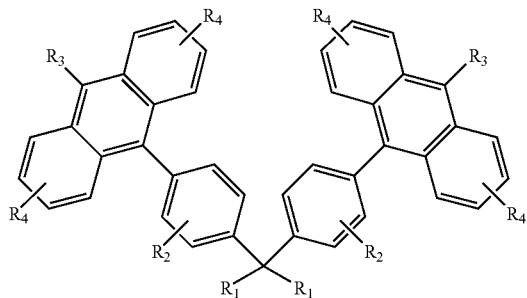

wherein $R_1$ is independently selected from the group consisting of an alkyl group, an aryl group, a heteroaryl group, an alkoxy group, an amino group, an alkyl amino group, and an aryl amino group; $R_2$ is independently selected from the group consisting of hydrogen, and an alkyl group; $R_3$ is independently selected from the group consisting of hydrogen, an alkyl group, an alkoxy group, a halogen atom, and a cyano group; and, $R_4$ is independently selected from the group consisting of hydrogen, an alkyl group, an aryl group, a heteroaryl group, an alkoxy group, a halogen atom, and a cyano group.

9. The display device according to claim 8, wherein $R_1$ is independently selected from the group consisting of alkyl group having 1 to 10 carbon atoms, an alkyl group having 1 to about 10 carbon atoms wherein at least one of said $R_1$ alkyl groups comprises one or more halogen atoms, an aryl group having about 6 to about 30 carbon atoms, a heretoaryl group having about 5 to about 24 carbon atoms, and an alkoxy group having 1 to about 24 carbon atoms; $R_2$ is independently selected from the group consisting of hydrogen, and an alkyl group having 1 to about 10 carbon atoms; and $R_3$ is independently selected from the group consisting of hydrogen, an alkyl group having 1 to about 10 carbon atoms, an alkoxy group having 1 to about 24 carbon atoms, and a halogen.

10. The display device according to claim 8, wherein $R_1$ is an alkyl group having 1 to about 10 carbon atoms; $R_2$ is independently selected from the group consisting of hydrogen, and an alkyl group having 1 to about 10 carbon atoms; and $R_3$ is independently selected from the group consisting of hydrogen, and an alkyl group having 1 to about 10 carbon atoms.

11. The display device according to claim 8, wherein $R_1$ is independently selected from the group consisting of methyl, ethyl, propyl, isopropyl, isobutyl, butyl, tert-butyl, trifluoro methyl, methoxy, ethoxy, tert-butoxy, butoxy, phenyl, and tert-butyl phenyl; $R_2$ is independently selected from hydrogen, methyl, ethyl, propyl, and butyl; and $R_3$ is independently selected from hydrogen, methyl, ethyl, propyl, isopropyl, isobutyl, butyl, tert-butyl, methoxy, ethoxy, butoxy, and tert-butoxy.

12. The display device according to claim 8, wherein $R_1$ is selected from the group consisting of an alkyl group having from about 1 to about 10 carbon atoms, and a halogenated alkyl group having from about 1 to about 10 carbon atoms; $R_2$ is hydrogen; and $R_3$ is hydrogen.

13. The display device according to claim 8, wherein the light-emitting material is selected from the group consisting of

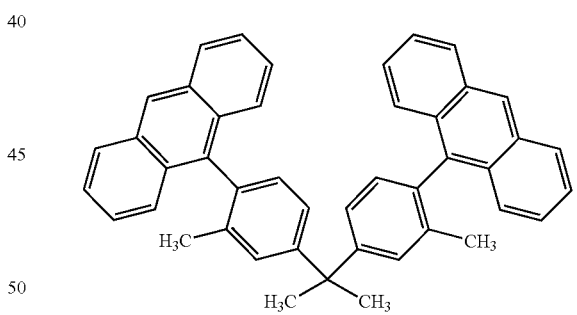

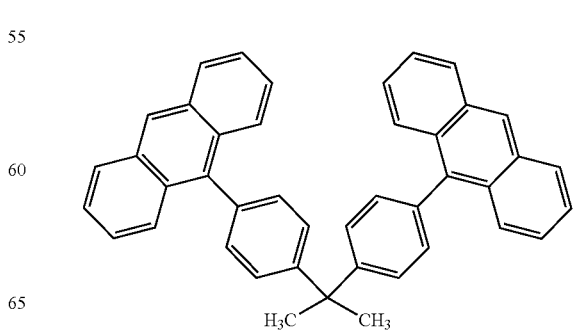

-continued
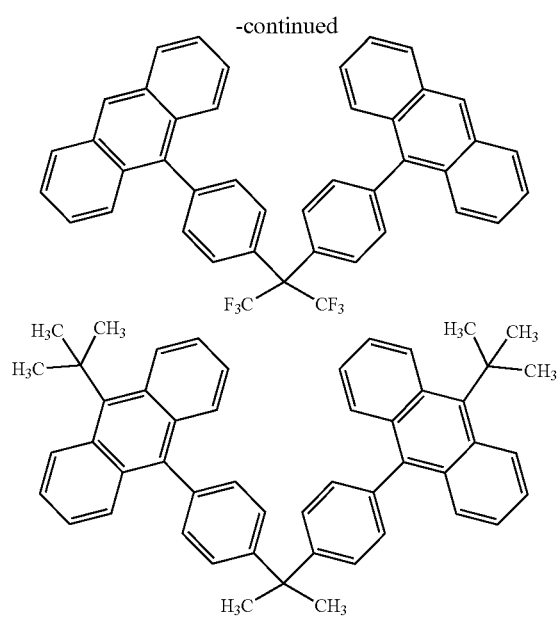
-continued
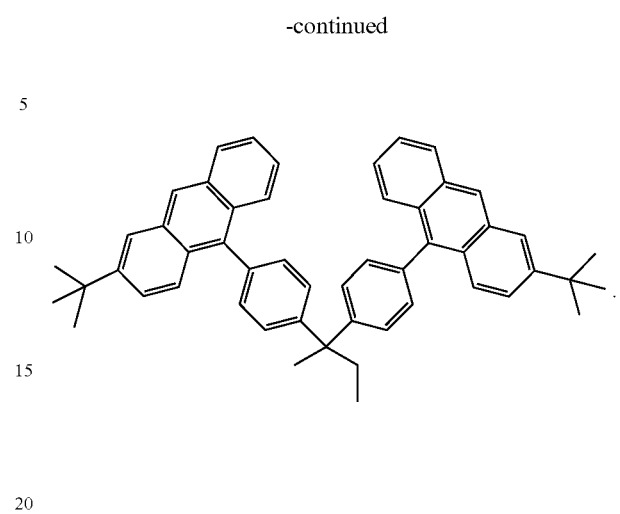
* * * * *